United States Patent
Berdichevsky et al.

(10) Patent No.: US 10,372,845 B1
(45) Date of Patent: Aug. 6, 2019

(54) SCATTEROMETRY SYSTEM AND METHOD

(71) Applicant: Nova Measuring Instruments Ltd., Rehovot (IL)

(72) Inventors: Ruslan Berdichevsky, Rishon LeZion (IL); Eyal Grubner, Holon (IL); Shai Segev, Yahud (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 560 days.

(21) Appl. No.: 14/927,850

(22) Filed: Oct. 30, 2015

(51) Int. Cl.
*G01N 21/95* (2006.01)
*G06F 17/16* (2006.01)
(Continued)

(52) U.S. Cl.
CPC ..... *G06F 17/5009* (2013.01); *G01N 21/9501* (2013.01); *G06F 17/16* (2013.01); *G01N 2021/4735* (2013.01)

(58) Field of Classification Search
CPC ..... G06F 17/5009; G06F 17/16; G01N 21/49; G01N 21/9501; G01N 2021/4735
(Continued)

(56) References Cited

U.S. PATENT DOCUMENTS

| | | | | |
|---|---|---|---|---|
| 2002/0033954 A1* | 3/2002 | Niu | ..... | G01B 11/0675 356/601 |
| 2004/0176928 A1* | 9/2004 | Johnson | ..... | G01B 11/24 702/182 |

(Continued)

OTHER PUBLICATIONS

Tsang, L., & Kong, J. A. (2001). Scattering of Electromagnetic Waves, Advanced Topics, vol. 3. Hoboken. pp. 1-4. (Year: 2001).*
(Continued)

*Primary Examiner* — Kamini S Shah
*Assistant Examiner* — John E Johansen
(74) *Attorney, Agent, or Firm* — Alphapatent Associates, LTD; Daniel J. Swirsky

(57) ABSTRACT

A method and system are presented for use in scatterometry analysis for a patterned structure. According to this technique, a model of a patterned structure is provided comprising a selected number of virtual segment data pieces indicative of a respective number of segments of the patterned structure along Z-axis through the structure. Each of the segment data pieces is processed for determining a matrix $[\Omega_n]$ comprising Z-axis derivatives of electromagnetic fields' response of the segment to incident field based on Maxwell's equations' solution, and transforming this matrix $[\Omega_n]$ into an approximated response matrix $[\wedge_n]$ corresponding to the electromagnetic field interaction between two different points spaced along the Z-axis. The transformation is preferably carried out by a GPU, and comprises embedding said matrix $[\Omega_n]$ in a series expansion of said matrix exponential term $[\wedge_n]$. Then, the approximated response matrices $\{[\wedge_n]\}$ for all the segment data pieces are multiplied for determining a general propagation matrix $[\wedge]$, which is utilized to determine a scattering matrix for the patterned structure. The multiplication may also be performed by GPU.

19 Claims, 5 Drawing Sheets

(51) Int. Cl.
  *G06F 17/50* (2006.01)
  *G01N 21/47* (2006.01)
(58) Field of Classification Search
  USPC .............................................................. 703/1
  See application file for complete search history.

(56) References Cited

U.S. PATENT DOCUMENTS

| 2008/0224930 | A1* | 9/2008 | Chizhik | ............... | G01C 21/206 |
| | | | | | 342/417 |
| 2013/0144560 | A1* | 6/2013 | Pisarenco | ............... | G01N 21/47 |
| | | | | | 702/189 |
| 2016/0283618 | A1* | 9/2016 | Levola | ................ | G06F 17/5009 |

OTHER PUBLICATIONS

Shirasaki "Scatterometry simulator using GPU and Evolutionary Algorithm" Metrology, Inspection, and Process Control for Microlithography XXV, Proc. of SPIE. 7971:79711T1-79711t7 (2011).
Tong et al "Computation Improvement for the Rigorous Coupled-wave Analysis with GPU" 2102 Fourth International Conference on Computational and Information Sciences, 17-19 : 123-126 (Aug. 2012).
Wei et al "Parallel computing for application in rigorous coupled-wave analysis" 2102 Fifth International Symposium on Computational Intelligence and Design (ISCID), vol. 2, 28-29 :186-189 (Oct. 2012).

* cited by examiner

SCATTEROMETRY SYSTEM AND METHOD

TECHNOLOGICAL FIELD

The invention is in the field of metrology and more particularly relates to systems and method for scatterometry based metrology and analysis of articles.

BACKGROUND

Scatterometry techniques are widely used for metrology on patterned structures (OCD) e.g. a semiconductor wafer (wafer/die), which may include plurality of different patterns. In these techniques, scattering response signal (signature) of a patterned structure e.g. on the semiconductor wafer (e.g. a test structure located in scribe lines, or a patterned structure in die) could be compared with simulated signal(s) obtained using one or more scatterometry models (simulation) which provide prediction about the scatterings response signal(s) expected from a patterned structure. A best fit condition between the measured scattering response and the predicted ones is used for determining the structure parameters.

Techniques for obtaining/calculating simulated signal from scatterometry models of a patterned structure could be based on for example the Rigorous Coupled-Wave Analysis (RCWA) technique. RCWA is a semi-analytical method in computational electromagnetics that may be applied to simulate scattering from periodically patterned structures. In the RCWA technique, signals are presented in the Fourier-space as a sum of spatial harmonics.

The scatterometry model provides a physical representation of a patterned structure enabling to predict (simulate) scattering response signal from the structure depending on parameters of the structure and metrology system (e.g. measurement scheme, defined by illumination and/or detection conditions). Based on the model, a set of Scatterometry (Reflectance) matrices is calculated for a desired parametric space. The Scatterometry (Reflectance) matrices are indicative of information on scatterings response signal (e.g. reflectivity) from the structure depending on the structure parameters and the measurement scheme. As indicated above, the measurement scheme is defined by illumination and/or detection conditions, such as detection of one or more specific diffraction orders, polarizations, etc. For spectral based techniques, such as Spectral Reflectometers or Spectral Ellipsometers, the Scatterometry Matrix is calculated per wavelength. The measurement scheme used in OCD scatterometry could be of any type, e.g. Spectral Ellipsometry (SE), Spectral Reflectometry (SR) (including polarized SR), angle-resolved scatterometry, etc. and combinations thereof.

Thus, Scatterometry matrix simulating the scattering (e.g. generally meaning reflection and/or transmission, and/or absorbance) of a particular patterned structure is obtained and further the best fit condition is used to determine the parameters of interest in the structure.

Certain known in the art techniques use graphics processing units (GPUs) in an attempt to improve the computational efficiency the RCWA based technique. For instance the publication "*Scatterometry simulator using GPU and Evolutionary Algorithm*" by Hirokimi Shirasaki (see *Metrology, Inspection, and Process Control for Microlithography XXV, Proc. of SPiE Vol.* 7971, 797117) suggests speeding up spectroscopy calculation and optimization algorithm systems by parallel computing using GPU. The publication "*Computation Improvement for the Rigorous Coupled-wave Analysis with GPU*" by Jing Tong and Shuqiang Chen, (2012 Fourth International Conference on Computational and Information Sciences, 17-19 Aug. 2012, pp. 123-126) suggests using a GPU for processing matrix operations to obtain Scatterometry solutions based on RCWA technique. Also, in the article "*Parallel computing for application in rigorous coupled-wave analysis*" by Xvlong Wei and Shuqiang Chen (2012 Fifth International Symposium on Computational Intelligence and Design (ISCID), Volume 2, 28-29 Oct. 2012, pp. 186-189), a parallel computing method is presented for RCWA which utilizes hybrid computation using GPU with CPU.

GENERAL DESCRIPTION

Scatterometry techniques are widely used in metrology on patterned structure such as semiconductor wafers.

With the development of semiconductor devices, the critical dimensions (CD) of features thereof are reduced to small sizes (e.g. the CD's in contemporary devices are in the order of 10 nanometer (nm) and even less). Scatterometry based techniques applied to complicated patterned structures (patterned structures itself could be very complicated, and characterized by large number of parameters) with such small CDs require use of complex and accurate scatterometry models to predict (simulate) the theoretical radiation scattering response of the structure. However, processing such complex and accurate scatterometry models is highly demanding in terms of the computation power and time requirements.

As indicated above, certain known techniques suggest improving the computational efficiency and reducing the computation time duration by exploiting the parallel computational abilities of GPUs.

Differently from CPUs, which excel in carrying out serial processing procedures and integer operations, GPUs excel in parallel processing procedures and in floating point operations. This makes GPUs ideal for computation of matrix operations such as matrix multiplications.

However, as described below, conventional processing of scatterometry models and calculating (Scattering Matrix) simulated signal (signature) involve operations such as matrix eigen decomposition, which are computationally intensive tasks for which using GPUs has no advantage (in fact, carrying out these operations is often considered more suited for CPUs). Therefore, in many cases, conventional techniques that use GPUs do not provide significant advantage in terms of the computational efficiency and time required to process scatterometry models.

It should be understood that processing of the scatterometry model is aimed at generating a corresponding simulated (modeled) scattering matrix for a point in a parametric space with respect to parameters of the structure. Thus, representing the entire parametric space including multiple parameters requires a corresponding set of the scattering matrices. The scattering matrices are then used for generating simulated (predicted) optical responses of a corresponding (modeled) patterned structure, for one or more given measurement conditions, such as illumination condition and/or detection condition (e.g. polarization, diffraction order(s)).

The present invention provides a novel technique for processing scatterometry models of article patterned structure (at times referred to in the description below as a "test site"), by using parallel computational abilities of GPU architecture processors. According to the invention, GPU is used for obtaining (calculating) Scatterometric matrix that contains "full" information about any electromagnetic response of the structure. By further transforming this information taking into account one or more parameters/conditions of the measurement scheme, the simulated response from the structure for point in parametric multi-dimensional space can be obtained.

Typically, the scatterometry model comprises data indicative of a profile used for predicting a radiation response (intensity versus wavelength) from a patterned structure. This profile information is expressed as a set of stacked slices/segments of material, where each slice is defined by width, height, index of refraction, etc. The profile can be made arbitrarily smooth by including a sufficient number of slabs. The profile modeled as a stack of slices (each with a specific width, height, and complex refractive index) provides a profile resolution determined by the number of slices. The calculation efficiency requires the use of a minimum number of slices, and therefore by properly adjusting the height and width of each slice, any arbitrary profile can be represented with a minimum number of slices.

This technique of modeling a patterned structure is described for example in U.S. Pat. No. 5,963,329, which is incorporated herein by reference.

The present invention utilizes such technique of scatterometry modeling a patterned structure by a predetermined (selected) number of virtual data pieces corresponding to successive slices/segments/regions of the patterned structure along Z-axis (lateral slices). Such virtual segment data piece is indicative of dielectrical properties and geometry of the respective segment/slice. In the description below, the technique of modeling the patterned structure by a predetermined number of slices is at times referred to as "segmenting" technique.

The technique of the present invention provides a novel approach for processing the virtual segment data pieces to determine electromagnetic propagation matrix for each segment/slice, and combining the electromagnetic fields of all the slices into a "full" or "general" propagation matrix by multiplication, and thereby determining the scattering matrix of the patterned structure. This scattering matrix is then used to determine a corresponding theoretical (predicted/simulated) response signature/signal. Such signature is typically determined as a function of at least one parameter of the measurement scheme, e.g. wavelength.

According to a broad aspect of the present invention, there is provided a method for use in scatterometry analysis for a patterned structure, comprising:

(a) providing a scatterometry model of a patterned structure comprising a selected number of virtual data pieces indicative of a respective number of segments of the patterned structure along Z-axis through the structure; and (b) Processing each of the virtual segment data pieces, said processing comprising:
  i) determining a matrix $[\Omega_n]$ comprising Z-axis derivatives of electromagnetic fields' response of the segment to incident field based on Maxwell's equations' solution;
  ii) transforming said matrix $[\Omega_n]$ into an approximated response matrix $[\wedge_n]$ corresponding to the electromagnetic field interaction between two different points spaced along the Z-axis, said transforming comprising embedding said matrix $[\Omega_n]$ in a series expansion of said matrix exponential term $[\wedge_n]$;

(c) determining a general propagation matrix $[\wedge]$ by carrying out multiplication of the approximated response matrices $\{[\wedge_n]\}$; and (d) utilizing the general propagation matrix $[\wedge]$ to determine a scattering matrix for the patterned structure.

It should be noted that the term "Z-axis" should be interpreted broader, corresponding to any axis through the structure, and not only vertical axis.

In the above method, at least the step (ii) is carried out by a GPU architecture processor. Also, the GPU architecture processor can be used for performing at least steps (ii) and (c). This may be a standard GPU, general purpose GPU (GPGPU), and a Many-Integrated-Core Architecture (MIC) processor, etc.

In the above method, the series expansion stage of processing may include at least one of Taylor Expansion and polynomial expansion.

The method may further include application of data indicative of a measurement scheme (at least one illumination and/or detection parameter or condition) to the scattering matrix, thereby obtaining simulated scatterometry response signals from the patterned structure corresponding to the model. The at least one of illumination and detection conditions comprises at least one of polarization and diffraction order being collected.

The scatterometry model typically comprises a set of structure parameters spanning a certain parametric space. The scattering matrix of the pattern structure corresponds to a point in the parametric space defined by the model. The determination of the scattering matrix may be carried out for a plurality of points in the parametric space respectively, thereby obtaining data indicative of a plurality of simulated scattering response signals for the plurality of points respectively.

The method may further comprise comparing measured scatterometry response signals of the patterned structure with the simulated scattering response signals, and determining one or more parameters of the structure based on a best fit condition.

Typically, scattering matrix corresponds to an illuminating wavelength, and the above-described processing is carried for each of multiple (generally, at least two) illuminating wavelengths.

In the above method, the determination of the scattering matrix may utilize an impedance matrix of media surrounding the patterned structure and the general propagation matrix.

In another broad aspect, the present invention provides a novel technique which can also be used in real time during measurements (a so-called "online" metrology mode) to optimize the previously selected scatterometry model used for determination of the structure parameters. There are generally two approaches, one based on using a preliminary generated library of simulated response signals (off-line mode) and the other being Real Time Regression (RTR) technique used for example for on-line optimization of the model parameters to improve the fit/match between the simulated and measured signatures.

The GPU architecture processor is used to efficiently compute scattering matrix for a modeled structure (patterned structure) used for simulating the response/signal/signature therefrom, and a CPU architecture processor is used to efficiently carry out the model parameters optimizations to fit the Scatterometry model to the measured data.

According yet another broad aspect of the invention, it provides a system for use in scatterometry analysis of patterned structures, comprising:
  a data input module for receiving input data comprising a scatterometry model including a selected number of virtual data pieces indicative of a respective number of segments of a patterned structure along Z-axis through the structure;

a matrix data processing module configured for processing each of the segment data pieces and determining a matrix $[\Omega_n]$ comprising Z-axis derivatives of electromagnetic fields' response of the segment to incident field based on Maxwell's equations' solution, and transforming said matrix $[\Omega_n]$ into an exponential term $[\wedge_n]$ corresponding to electromagnetic field interaction between two different points spaced along the Z-axis, said transforming comprising embedding said matrix $[\Omega_n]$ in a series expansion of said matrix exponential term $[\wedge_n]$;

a matrix multiplication processing module adapted for multiplying the approximated response matrices $\{[\wedge_n]\}$ corresponding to all the segment data pieces and determining a general propagation matrix $[\wedge]$, and a scattering matrix generator configured for utilizing the general propagation matrix $[\wedge]$ and determining a scattering matrix of the patterned structure.

According to yet further aspect of the invention, there is provided a program storage device readable by machine, tangibly embodying a program of instructions executable by the machine to perform the above method for use in scatterometry analysis for a patterned structure.

The invention, in its yet another broad aspect, provides a computer program product comprising a computer useable medium having computer readable program code embodied therein for use in scatterometry analysis for a patterned structure. The computer program product comprises computer readable program code for causing the computer to carry out the steps of the above described method of the invention.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

DETAILED DESCRIPTION OF EMBODIMENTS

Figure 1A:
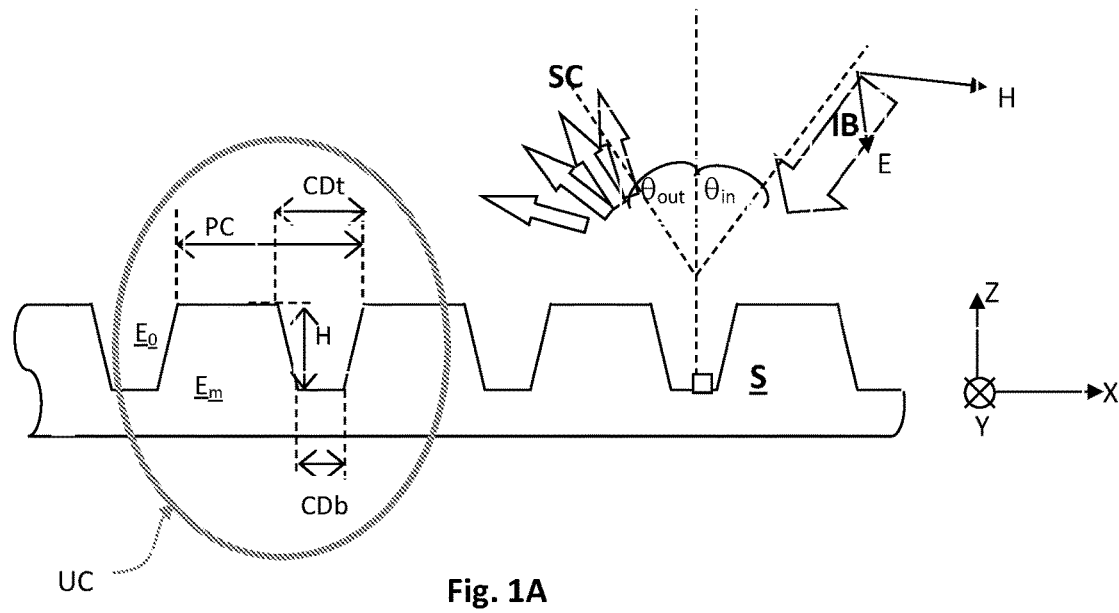
FIG. 1A illustrates a side cross-sectional view of a patterned structure S (at times referred to as sample (die) or test-site), which is to be measured by Scatterometry.

FIG. 1A illustrates a simplified side cross-sectional view of a patterned structure S (e.g. located in a test site), which is to be measured by metrology techniques, and more specifically by utilizing Scatterometry. The patterned structure S presents a certain spatial distribution of dielectric properties $\varepsilon$ (which distribution is marked/illustrated in the example of FIG. 1A by $\varepsilon^0$ and $\varepsilon^1$), which is associated with the locations and material compositions of the pattern features in the patterned structure S.

Based on a scatterometry model that is indicative of the spatial distribution of the dielectric properties in the patterned structure S, certain reflection/scattering properties (e.g. scattering matrix R) can be simulated, and may be further used to determine/predict scatterings response signals of the patterned structure to illumination thereof. The scatterings response signals are indicative of the way incident radiation IB (e.g. optical-radiation/light beam) would be returned (reflected/scattered) from the patterned structure S. Usually, the Scatterometry model represents patterned structure that corresponds (correlates) with real structure of interest (e.g. in an actual die). Accordingly, measurement of one or more parameters of actual patterned structures can be achieved by utilizing the predicted scattering response signals/data of the patterned structures within the parametric space which is defined/spanned by the model, and determining a point in the parametric space which scattering response signals best fit the measured scattering response signal of the patterned structure.

By fitting measured signals with simulated scattering response signals, values of parameters of interest of the patterned structure (e.g. CDs, SWAs, depths/heights, rounding's (top/bottom), etc.), can be determined/measured. Measured parameters can be used for process control, e.g. for feedback, feed forward, full automatic process control, etc.

In this example, the patterned structure S is a periodic-pattern structure (e.g. one/two dimensional grating structure with pitch P and grooves height H) with features having critical dimension (CD) ranging from $CD_b$ (the critical dimension in the bottom surface of the grating) to $CD_t$ (the critical dimension in the top surface of the grating).

It should, however, be understood, that the technique of the present invention is not limited to periodic structures (such as gratings), as well as not limited to any specific pattern, and may be used to simulate scatterings response signals from various types of patterned structures which may be of arbitrary complexity, and which may include plurality of material layers comprised of different structures and/or different material compositions.

As indicated above, simulating the scattering matrix R (e.g. reflection/transmission matrix) of a patterned structure S is generally computationally intensive task, which is one of the bottle necks of Scatterometric metrology of patterned structures, due to the exponential growth in the complexity of structures which are used in the semiconductor industry and the small critical dimensions of the features of contemporary semiconductor devices/samples that are to be measured. Indeed, OCD Scatterometry became one of the most effective non-destructive techniques, specifically because other measurement/metrology techniques are either destructive (e.g. CD-SEM) or of low throughput (e.g. X-ray based techniques).

The present invention provides a novel technique (systems and methods) for performing Scatterometry modeling/simulation used further for measurements, with reduced computational requirements and in shorted time as compared to conventional Scatterometry modeling/techniques.

Figure 2A:
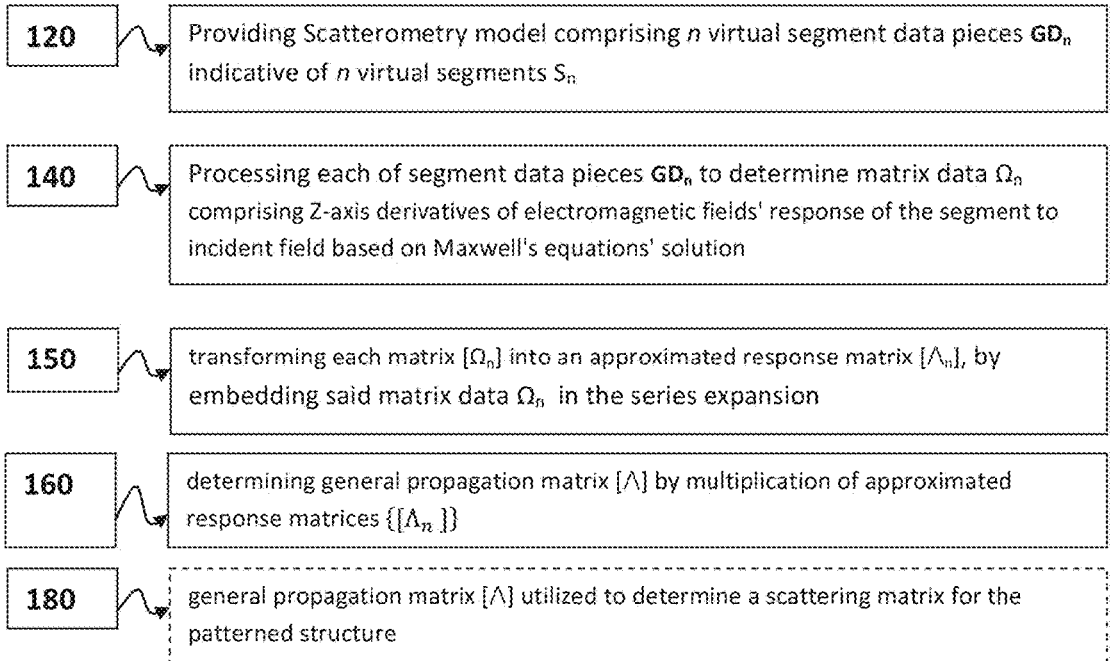
FIG. 2A is a flow chart illustrating a method according to an embodiment of the present invention for calculating the electromagnetic (EM) propagation matrix through a segment of the patterned structure.

FIG. 2A is a flow chart illustrating a method 100 according to an embodiment of the present invention for modeling the transfer matrix scattering/reflection/transmission matrix R of a segment (e.g. region) $S_n$ of the patterned structure S.

Operation 120 includes providing a scatterometry model of a patterned structure including virtual data pieces $GD_n$ indicative of n virtual segments/slices $S_n$ (n is an index of the segment) of the patterned structure S arranged along Z-axis through the structure. As noted above, this technique is generally known, and therefore need not be described in details except to note the following: The segment data pieces $GD_n$ are generally indicative of the spatial distribution of dielectric properties $\varepsilon_n$ in the respective segments $S_n$. To this end the, segment data piece $GD_n$ may be indicative of the pattern/layout/critical dimensions of features in the segment $S_n$ (for instance in case the segment includes grating layout of features, and the material composition of the features and spacings between them). Accordingly, the spatial distribution of dielectric properties in the segment $S_n$ can be derived/provided from its respective segment data piece $GD_n$.

Operation 140 includes processing each of the virtual segment data piece $GD_n$ (more specifically processing the spatial distribution of dielectric properties $\varepsilon_n$ in the segment $S_n$) to determine a matrix data $\Omega_n$ comprising Z-axis derivatives of electromagnetic fields' response of the segment to incident field based on Maxwell's equations' solution.

Operation 150 includes transformation of each matrix $[\Omega_n]$ into an approximated response matrix $[\wedge_n]$. This approximated response matrix $[\wedge_n]$ corresponds to the electromagnetic field interaction between two different points spaced along the Z-axis. Such transformation includes embedding the matrix $[\Omega_n]$ in a series expansion of the matrix exponential term $[\wedge_n]$.

In this regards it should be noted that Maxwell's equations can be presented in the so called semi-analytical form as specified in Eq. 1 below.

$$\frac{\lambda}{2\pi j}\frac{d}{dz}\begin{pmatrix} E_n^X(z) \\ E_n^Y(z) \\ H_n^X(z) \\ H_n^Y(z) \end{pmatrix} = \Omega_n \begin{pmatrix} E_n^X(z) \\ E_n^Y(z) \\ H_n^X(z) \\ H_n^Y(z) \end{pmatrix} \qquad \text{Eq. 1}$$

where $\lambda$ is the wavelength being used; E and H are respectively electric and magnetic fields, and j is the imaginary unit.

As will be readily appreciated by those versed in the art, this presentation of Maxwell's equations can be derived by application of Fourier transform (FT) to the matrix presentation of Maxwell's equations with respect to two lateral axes/directions, X and Y, while without application of FT with respect to the longitudinal axis/direction Z. Accordingly, the left side of the equation (1) remains a differential term with respect to Z, while the left side is an algebraic term (in which the differentiation with respect to X and Y are substituted by the lateral coefficients $K_X$ and $K_Y$ of the wave vector K).

Eq. 1 is actually a matrix wave equation derived from the Maxwell's equations. Eq. 2 below is a wave form solution to the differential Maxwell's equation shown Eq. 1 (more specifically, a plane wave solution). This equation is indicative of the electromagnetic propagation matrix (propagation matrix) of electric E and magnetic H fields through the segment $S_n$ of the sample S (e.g. along the Z direction), i.e. from the distribution of the electric and magnetic fields, $E_{n-1}$ and $H_{n-1}$, at one side (e.g. bottom) of the segment $S_n$ to the distribution of the electric and magnetic fields, $E_n$ and $H_{n-1}$ at the opposite side (e.g. top) of the segment $S_n$ (where n is the segment's index).

$$\begin{pmatrix} E_n^X \\ E_n^Y \\ H_n^X \\ H_n^Y \end{pmatrix} = \wedge_n \begin{pmatrix} E_{n-1}^X \\ E_{n-1}^Y \\ H_{n-1}^X \\ H_{n-1}^Y \end{pmatrix} \qquad \text{Eq. 2}$$

where $\wedge_n$ is a matrix exponential term presenting an approximation matrix (which is also at time referred to below as propagation matrix or matrix exponential term), which is indicative of the way the electric E and magnetic H fields are transferred through the segment $S_n$ of the sample S, i.e. corresponds to the electromagnetic interaction between two different points spaced along the Z-axis (an axis of propagation of the electromagnetic response of the structure). The approximation matrix is given by:

$$\wedge_n = \exp\left\{-j\left(\frac{\omega}{c}\right)h_n\Omega_n\right\}$$

Here, $h_n$ is segment height, and $\Omega_n$ is a matrix, which is derived by application of Fourier transform to the spatial distribution of dielectric properties $\varepsilon_n$ in the segment $S_n$, wherein the Fourier transform is applied with respect to the lateral X and Y directions. As will be appreciated by those versed in the art and further explained below, the segment $S_n$, and so is the spatial distribution of its dielectric properties $\varepsilon_n$, may be considered homogeneous with respect to the Z direction.

It should be understood that the dielectric properties $\varepsilon_n$ generally depend on the wavelength(s) $\lambda$ and $GD_n$. Although for clarity in the following the dielectric properties are indicated by $\varepsilon_n$, it should be understood that $\varepsilon_n$ actually depend upon (or is a function of) the above indicated parameters and should be considered as $\varepsilon_n \equiv \varepsilon_{n(X,Y)}, \lambda, GD_n$. Accordingly, matrix $\Omega_n$ may be a function of the effective wavelength(s) $\lambda$ of the incident radiation, as well as of its wave vector components $K_X$ and $K_Y$, namely $\Omega_n \equiv \Omega_n(K_X, K_Y, \lambda)$.

In this regards, it should be noted that in some cases the virtual segment data piece $GD_n$ includes the spatial distribution of the dielectric properties $\varepsilon_n$ of the segment already presented in the Fourier space. In this case, operation 140 may include extracting and/or constructing the matrix $\Omega_n$ from the segment data piece $GD_n$.

In cases where the segment data piece $GD_n$ is indicative of the spatial distribution of the dielectric properties $\varepsilon_n$ in real space, operation 140 may include determining the spatial distribution of the dielectric properties $\varepsilon_n$ from the information included in the segment data piece $GD_n$ (e.g. by processing data indicative of the layout of features in the segment $S_n$ and the dielectric properties of their material compositions as will be appreciated by those versed in the art). Then, operation 140 includes applying FT (e.g. using FFT) to the spatial distribution of the dielectric properties $\varepsilon_n$ with respect to the X and Y axes to obtain the matrix $\Omega$. This may be based for example on the following equation for $\Omega_n$:

$$\Omega_n = \begin{pmatrix} & 0 & & \dfrac{c^2}{\omega^2}k_x\dfrac{1}{\epsilon_n}k_y & 1-\dfrac{c^2}{\omega^2}k_x\dfrac{1}{\epsilon_n}k_x \\ & & & -1+\dfrac{c^2}{\omega^2}k_y\dfrac{1}{\epsilon_n}k_y & -\dfrac{c^2}{\omega^2}k_y\dfrac{1}{\epsilon_n}k_x \\ -\dfrac{c^2}{\omega^2}k_xk_y & -\epsilon_n+\dfrac{c^2}{\omega^2}k_xk_x & & & 0 \\ \epsilon_n-\dfrac{c^2}{\omega^2}k_yk_y & \dfrac{c^2}{\omega^2}k_yk_x & & & \end{pmatrix} \quad \text{Eq. 3}$$

where $$\frac{c}{\omega} = \frac{\lambda}{2\pi}$$

Conventional implementations of Scatterometry modeling techniques, such as Rigorous Coupling Wave Analysis (RCWA), turn to solving matrix exponential equation, such as Eq. 2, by diagonalizing (Eigen decomposition) the matrix in the exponent $\Omega$. In this case, once diagonalizing the matrix $\Omega_n$ and finding its Eigen vectors $\{V_i\}$ and its Eigen values the exponential term $\wedge_n$ becomes $$\Lambda_n = [V]\exp\left\{-j\left(\frac{\omega}{c}\right)h_n[\kappa]\right\}[V]^{-1} = \quad \text{Eq. 4}$$

$$[V]\begin{bmatrix} e^{-j(\frac{\omega}{c})h_n\kappa_1} & 0 & \cdots & 0 \\ 0 & e^{-j(\frac{\omega}{c})h_n\kappa_2} & & 0 \\ \vdots & & \ddots & \vdots \\ 0 & 0 & & e^{-j(\frac{\omega}{c})h_n\kappa_I} \end{bmatrix}[V]^{-1}$$

where [V] is a block matrix with the Eigen vectors $\{V_i\}$ in its columns and form [$\kappa$] is a diagonal matrix with the Eigen values $\{\kappa_i\}$ in its diagonal. Since [$\kappa$] is a diagonal matrix the term $$\exp\left\{-j\left(\frac{\omega}{c}\right)[\kappa]\right\}$$

is also diagonal matrix with the elements $$\exp\left\{-j\left(\frac{\omega}{c}\right)\kappa_i\right\}$$

in the diagonal cells (i,i) of the matrix.

However, the inventors of the present invention have realized that Eigen decomposition of matrixes $\Omega$ for various wavelengths of radiation, this approach for Scatterometry modeling suffers from a need for significant computational resources and extended computational time durations. Indeed, having analyzed the efficiency and effectiveness of various types of processors with task dedicated configurations, such as digital signal processors (DSPs), graphical processing units (GPUs), and central processing units (CPUs) in performing this task of matrix diagonalization, the inventors have found that none of those architectures presents major improvement in terms of the required computational processing time.

Thus, certain embodiments of the present invention provides for reducing the computational load associated with matrix diagonalization, by using an approximation which reduces the exponential matrix term $\wedge_n$ into a series of matrix multiplications.

Operation 150 of method 100 includes embedding the virtual segment relating matrix $\Omega_n$ (which is the representation of the distribution of dielectric properties $\epsilon_n$ in the Fourier space as obtained in 140) within the series expansion approximating the matrix $\wedge_n$. More specifically, the series expansion may be a power series such as Taylor series or polynomial series taken up to a certain expansion order M. Such approximation of the exponential matrix term $\wedge_n$ is provided for example in Eq. 5.

$$\Lambda_n = \exp\left\{-j\left(\frac{\omega}{c}\right)\Omega_n\right\} \approx \sum_{m=0}^{M}\left[\frac{\left(-j\left(\frac{\omega}{c}\right)h_n\right)^m(\Omega_n)^m}{m!}\right] \quad \text{Eq. 5}$$

Then, operation 160 includes determining a general propagation matrix [$\wedge$] by carrying out multiplication of the approximated response matrices $\{[\wedge_n]\}$ in the series expansion provided in Eq. 5 with the proper wavelength $\lambda$.

Then, operation 180 may be performed by utilizing the general propagation matrix [$\wedge$] to determine a scattering matrix for the patterned structure.

According to certain embodiments of the present invention, the transformation computed in 160 (and possibly also multiplication operation 180) is/are performed by utilizing one or more Graphical Processing Unit (GPU) processors, or one or more processors with architecture similar to graphical processing unit. For example, employing and operating one or more standard GPUs, general purpose GPUs (GPGPUs), and/or Many-Integrated-Core Architecture processors (MICs) to perform the matrix calculations/multiplications. It should be understood that in the following, as well as in the appended claims, the term GPU architecture processor is used to generally refer to multi-core processors which have a plurality of processing cores, in the order of a few tens or more, preferably a few hundreds or more of processing cores.

In this regards it should be noted that the GPU architecture processor does not provide significant advantage and does not significantly shortens the computational time when employed for carrying out matrix diagonalization operations, such as that described for example with reference to Eq. 4 above. Therefore, known in the art attempts to employ GPUs for processing Scatterometry models, such as RCWA, had often resulted with no, or insignificant, performance improvement as compared to the performance achievable when using CPUs.

However, the GPU architecture processors are more particularly designed for efficient performance of floating point operations and matrix multiplications (wherein CPU are more tuned to integer operations). Also, GPUs employ SIMT (single instruction multiple thread) for scalar thread processing, wherein CPUs use SIMD (single instruction, multiple data) units for vector processing. As SIMT does not require the programmatic organization of the data into vectors, and it permits arbitrary branching behavior for threads. Accordingly, GPU architecture processors have significant performance advantage and significantly reduce the computational time required to perform the matrix multiplications, such as those of Eq. 5 above. Certain of the characterizing features of the GPU architecture are listed in Table 1 below in comparison to CPU architecture:

TABLE 1

| Processor | CPU Architecture | GPU Architecture | Ratio GPU/CPU |
| --- | --- | --- | --- |
| Transistors | About 4 billion | About 8 billion | ~X2 |
| Cores | 2-18 | Few thousand | ~X150 |
| Peak gigaflops (floating point operations per second) | About 200 gigaflops | About 1300 gigaflops | ~X7 |
| Memory Bandwidth | About 60 GBps | About 290 GBps | ~X5 |
| Vector Processing | SIMD | SIMT | |

In view of the above, the inventors of the present invention have found that significant reduction in the computational time needed for simulating Scatterometry matrices can be achieved by using power series approximation of the propagation matrix $\wedge_n$ as exemplified in Eq. 5 above and operating one or more GPU architecture processors to solve the matrix multiplications in said power series approximation. The GPU architecture processors process the matrix multiplication in parallel (e.g., using the SIMT type processing). This provides useful and accurate estimation of the propagation matrix $\wedge_n$ from which reflective/scattering properties (e.g. reflection/transmission matrix R) of the segment $S_n$ or of the entire patterned structure S can be determined with improved efficiency and accuracy and/or and shorter duration.

Figure 2B:
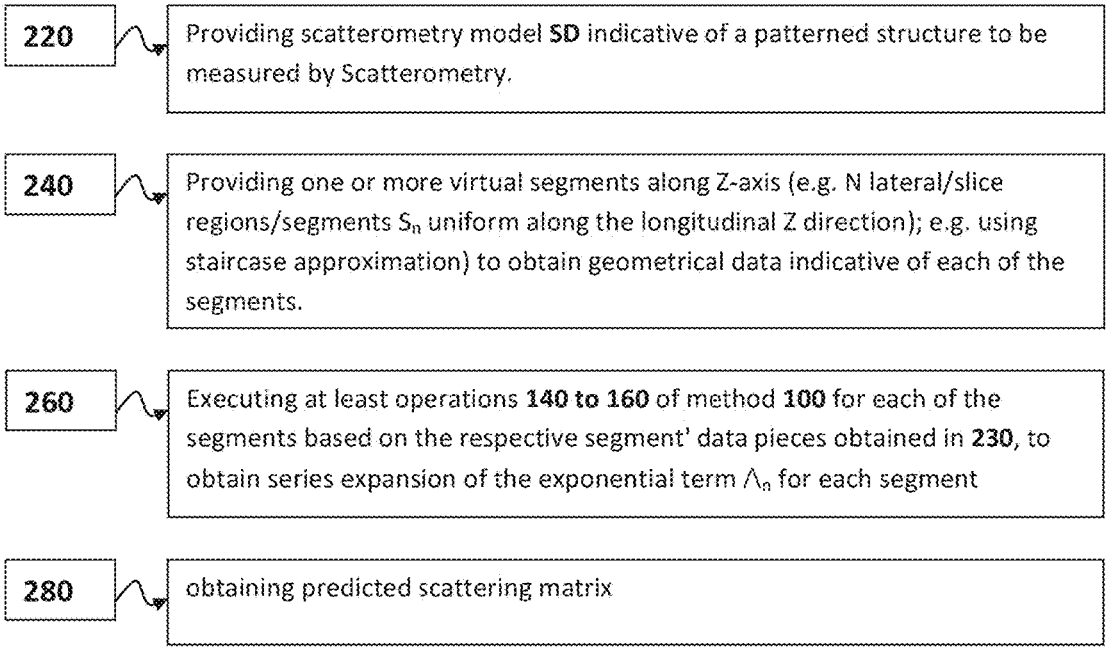
FIG. 2B is a flow chart illustrating a method according to an embodiment of the present invention for calculating the scattering matrix of the patterned structure.

FIG. 2B is a flow chart illustrating a method 200 for modeling the scattering (e.g. reflection/transmission) matrix R of the patterned structure S to predict and obtain the respective scattering response signature/signal of the structure.

Operation 220 of method 200 includes providing scatterometry model SD indicative of the patterned structure S, which reflection/scattering properties are to be modeled for Scatterometry measurements/metrology (i.e. for interpreting measured data). The patterned structure may generally be a three dimensional structure, such as semiconductor wafer/device, having arbitrary complexity. It may include a plurality (one or more) layers/regions of various/different material compositions and dopings, and the layers may include various arrangements of features/elements of the pattern which may be formed by various known in the art fabrication techniques (e.g. patterning, resists masks, dry/wet etching, material evaporation/growth, ion bombardments and/or other fabrication techniques). Accordingly, pattern features in the layers/patterned structure S may be distinguished from their surroundings in the patterned structure S by their material compositions, lattice structure, optical/dielectric properties, and/or other properties.

In order to enable estimation/determination of a scattering matrix of the patterned structure, the spatial distribution of dielectric properties ε (X,Y) in the patterned structure S is needed. To this end, the scatterometry model SD provided in 220 is indicative of the spatial distribution of dielectric properties ε(X,Y,Z) in the patterned structure S. For instance the scatterometry model SD may include any one or more of the following data, from which the spatial distribution of dielectric properties ε(X,Y,Z) can be determined:

Spatial distribution of dielectric properties ε(X,Y,Z) itself;
Geometry and layout of the patterned structure and/or of material layers/regions therein;
Geometry and layout of features in the patterned structure.
For example in case the patterned structure includes a grating structure, the CD (top/bottom CD), and the pitch and height of the grating.

Material data indicative of the dielectric properties of material compositions from which various layers/regions/features of the patterned structure are made. For example the material data may include the dielectric properties ε of the material composition in each region/layer of the patterned structure and/or the compositions/doping/lattice structure of the material composition of each region/layer for the patterned structure, from which the dielectric properties can be determined by using suitable reference data of materials.

Thus, the scatterometry model SD provides and/or may be processed in 220 to determine a spatial map of the distribution ε(X,Y,Z) of dielectric properties in the patterned structure S.

Operation 240 includes segmenting the scatterometry model SD into one or more, generally N, virtual segments $\{S_n\}_1^n$, such that the dielectric properties of each segment $\varepsilon_n(X,Y)$ are uniform (homogeneous) along the longitudinal Z axis, but may vary in the lateral X and Y directions.

In this connection, in some embodiments, operation 220 includes discretizing/quantizing the spatial map of the distribution ε(X,Y,Z) (e.g. pixelize it according to any suitable known in the art pixilation technique), and thereafter dividing the pixilated/quantized map of the dielectric properties ε(X,Y,Z) into segments $S_n$ which are homogeneous along the Z axis.

In some embodiments of the present invention, a so-called staircase approximation is used to pixelize and segment the dielectric properties map ε(X,Y,Z) into segments $S_n$ homogeneous along the Z axis.

Figure 1B:
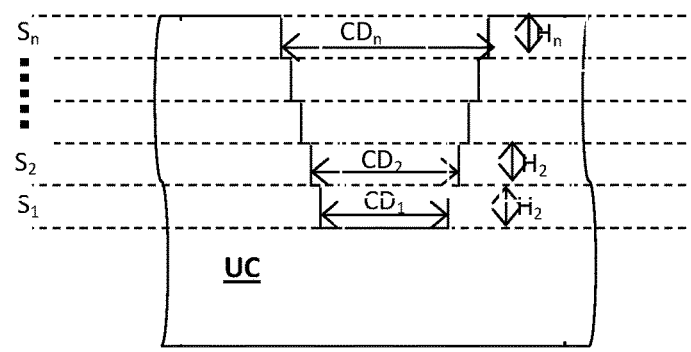
FIG. 1B is a side cross-sectional view showing the structure of a unit cell UC of the periodic pattern in the patterned structure.

For instance, in some embodiments, the following operations are carried out to segment the dielectric properties map ε(X,Y,Z) of the patterned structure. These operations are described with reference to FIGS. 1A and 1B:

(a) Optionally, the dielectric properties map ε(X,Y,Z) is processed to identify a certain repetitive unit cell UC (periodically repeated in the pattern along the lateral X and/or Y axes of the patterned structure). Such unit cell UC is exemplified in FIG. 1B.

(b) Then, the dielectric properties distribution map $\varepsilon_{UC}$(X,Y,Z) of the unit cell is extracted from the general dielectric properties map ε(X,Y,Z) of the patterned structure (e.g. based on the location and dimensions of the unit cell UC in the patterned structure S).

(c) Optionally, the dielectric properties distribution map $\varepsilon_{UC}$(X,Y,Z) is divided/sliced laterally into "natural" lateral layers/slices of different dielectric properties. In some cases, this is performed according to the Z coordinate of the locations interfaces/boundaries between different materials/layers in the patterned structure S (or in the unit cell UC).

(d) The dielectric properties distribution map $\varepsilon_{UC}$(X,Y,Z) of the "natural" lateral layers/slices (or more generally of the unit cell US or of the patterned structure S) is then pixilated/quantized.

(e) The pixilated dielectric properties distribution map $\varepsilon_{UC}$(X,Y,Z) of each "natural" lateral layers/slice (or more generally of the unit cell US or of the patterned structure S) is then divided (sliced) laterally into the segments $\{S_n\}$ which are in this case lateral slice regions that are homogeneous with respect to the Z axis (namely their spatial distribution/map of dielectric properties $\varepsilon_n$(X,Y) does not depend and is constant along the Z axis (this can be achieved for instance by slicing the pixilated/quantized dielectric properties distribution map $\varepsilon_{UC}(X,Y,Z)$ to slices extending no more than one pixel in the Z direction).

Thus, operation 240 provides the spatial distribution of dielectric properties $\varepsilon_n(X,Y)$ of each of the segments $\{S_n\}$.

In operation 260, the operations 140 to 160 of method 100 are executed/carried out for each of the virtual segments $\{S_n\}$ based on the respective segment data piece (e.g. based on the spatial distribution of dielectric properties $\varepsilon_n(X,Y)$ obtained in 230), to thereby obtain the series expansion of the matrix exponential term $\wedge_n$ (e.g. in accordance with Eq. 5), which represents the approximation matrix of the electric and magnetic fields through each of the segments $\{S_n\}$.

In operation 280, a scattering matrix R indicative of the reflection/scattering properties of the patterned structure S, is computed based on the approximation matrices $\wedge_n$ of the segments. More specifically, a general propagation matrix $\wedge$ indicative of the propagation of the electric E and magnetic H fields through the patterned structure S is computed, by multiplying the approximation matrixes $\wedge_n$ by one another in the order of the segments. The general propagation matrix $\wedge$ can be computed in accordance with Eq. 6, as follows:

$$\wedge = \prod_{n=1}^{N} \wedge_n \approx \prod_{n=1}^{N}\left[\sum_{m=0}^{M}\left[\frac{\left(-j\left(\frac{\omega}{c}\right)h_n\right)^m (\Omega_n)^m}{m!}\right]\right] \quad \text{Eq. 6}$$

The scattering/reflection matrix R of the patterned structure S may then be calculated by multiplying the general propagation matrix $\wedge$ by an impedance matrix Q representing the impedance of media surrounding the patterned structure, as follows:

$$\begin{pmatrix}A\\B\end{pmatrix} = \wedge * \begin{pmatrix}I\\Q_{base}\end{pmatrix} = \left[\prod_{n=1}^{N}\wedge_n\right]*\begin{pmatrix}I\\Q_{base}\end{pmatrix} \quad \text{Eq. 7}$$

where $Q_{base}$ is the impedance matrix of the base layer; and I is the unity matrix.

Then the scattering matrix is extracted as $$R = (A - Q_{top}^{-1}B)(A + Q_{top}^{-1}B)^{-1}$$

$Q_{top}$ is the impedance matrix of the top medium (sir in most cases).

As indicated with reference to operation 180 above, in some embodiments of the present invention, in operation 280 the computation of the general propagation matrix $\wedge$ and/or the scattering/reflection matrix R is carried out by operating one or more GPU architecture processors to compute the matrix operations/multiplications involved in this computation, as exemplified in Eq. 6 and/or 7 above. Accordingly, significant reduction in the computational time needed for determining/predicting the scattering matrix and the respective simulated response signal is achieved.

It should be noted that the simulated scattering response signal is obtained by applying data indicative of a measurement scheme to the scattering matrix R. Such measurement scheme is characterized by one or more illumination and/or detection conditions, including for example at least one of polarization and diffraction order of detection. It should be noted, that as described above, the scattering matrix corresponds to an illuminating wavelength, and the above described processing stages are performed for each of two or more illuminating wavelengths.

Figure 3:
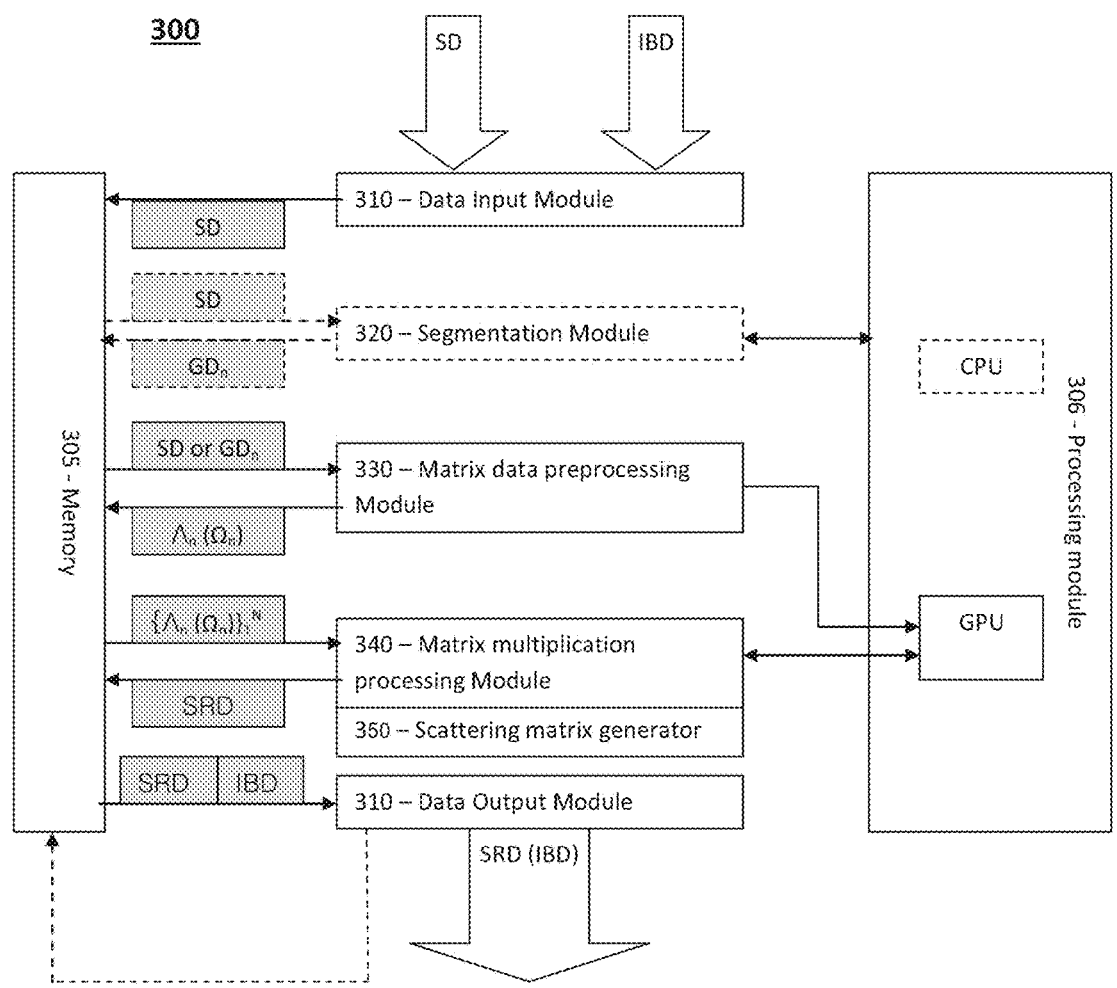
FIG. 3 is a block diagram of a Scatterometry simulation/modeling system 300 according to an embodiment of the present invention.

Reference is made to FIG. 3 showing a block diagram of a Scatterometry simulation/modeling system 300 according to an embodiment of the present invention. The system 300 is typically implemented as a computerized system including software, hardware, and/or firmware components/modules, configured and operable for carrying out the operations of methods 100 and/or 200 described above. To this end the system 300 includes inter alia a data processing module 306, including one or more processors with at least one GPU architecture processor, and a memory 305. For clarity, the blocks in the block diagram in the figure are selected to represent functional modules of the system, which can be implemented separately and/or by one or more software and/or hardware components.

In certain embodiments of the present invention, the system 300 includes a data input module 310, a matrix data preprocessing module 330, a matrix multiplication processing module 340, and a scattering matrix generator 350.

The data input module 310 is configured and operable for carrying out operations 120 or 220 as described with reference to methods 100 or 200 above. More specifically the data input module 310 is adapted for receiving scatterometry model SD indicative of distribution of dielectric properties $\varepsilon_n$ in at least one segment $S_n$ of the patterned structure S, and receiving a plurality of virtual segment data pieces indicative of a respective plurality of segments of a patterned structure along Z-axis through the structure.

The matrix data preprocessing module 330 is associated with (connectable to) the processor module 306 and adapted for processing the distribution of dielectric properties $\varepsilon_n$ of each segment $S_n$ of the patterned structure. More specifically, module 330 is preprogrammed for processing each of the segment data pieces to determine a matrix data $\Omega_n$ comprising Z-axis derivatives of electromagnetic fields' response of the segment to incident field based on Maxwell's equations' solution, and also preprogrammed for transforming the matrix $[\Omega_n]$ into an exponential term $[\wedge_n]$, as described above. The transformation of the matrix $[\Omega_n]$ includes embedding the matrix $[\Omega_n]$ in a series expansion of the matrix exponential term $[\wedge_n]$ exemplified/included in Eqs. 5, 6, or 7, above. To this end, the matrix data preprocessing module 330 is configured and operable for carrying out operations 140 and 150 of method 100 described above (or at least part of operation 260 of method 200 described above). It is understood that data (e.g. predetermined data) indicative of these equations may be stored in the memory 305 and utilized by the matrix multiplication processing module 340 to carry out this embedding operation.

The matrix data preprocessing module 330 may be configured and operable to determine said matrix data $[\Omega_n]$ for each segment $S_n$ by applying Fourier transform (FT) to the distribution of dielectric properties $\varepsilon_n$ of the segment with respect to the lateral spatial axes, X and Y, of the patterned structure S.

The matrix multiplication processing module 340 is adapted for multiplying the approximated response matrices $\{[\wedge_n]\}$ corresponding to all the segment data pieces and determining a general propagation matrix $[\wedge]$. The matrix data preprocessing module 330 (as well as the matrix multiplication processing module 340) may be part of the GPU architecture processor (e.g. standard GPU, general purpose GPU (GPGPU), and/or MIC processor). The general propagation matrix $[\wedge]$ can be used by the scattering matrix generator for obtaining signals indicative of the scattering response/signature and/or scatterings matrix R (e.g. reflection/transmission matrix) of the patterned structure S and/or of at least one of its segments Sn.

The data input module 310 may be adapted for obtaining measurement scheme data IBD indicative of one or more of the illumination and detection conditions (illuminating wavelength, and possibly also polarization, angle of incidence, diffraction order of the detection). Accordingly, the matrix data $\Omega_n$ of the virtual segment may be computed by the preprocessing module 330 as function of at least one parameter, e.g. $\lambda$, of the measurement scheme to determine the scattering matrix. In this case, the simulated response signal is obtained by applying the measurement scheme to the scatterings matrix R.

According to some embodiments of the present invention, the system includes segmentation module 320 configured and operable for processing the scatterometry model SD associated with the patterned structure S, to identify/divide/segment the pattern structure into virtual segments $S_n$ which are lateral slice regions of the patterned structure S in which the distribution of dielectric properties $\varepsilon_n$ is substantially homogeneous along the longitudinal axis Z. Accordingly, for each segment $S_n$, the segmentation module 320 extracts, and stores in memory 305, a segment data piece $GD_n$ which is indicative of the spatial distribution of the dielectric properties $\varepsilon_n$ of the respective segment $S_n$. In such embodiments, the matrix data preprocessing module 330 carries out the processing of the distribution of dielectric properties $\varepsilon_n$ for each of the segments $S_n$ to obtain said matrix data $\Omega_n$. Accordingly, the matrix multiplication processing module 340 utilizes these matrices $\Omega_n$ of the plurality of segment data pieces to calculate the general electromagnetic propagation matrix $\wedge$ of the patterned structure S (e.g. by operating GPU architecture processor based on computing the sequential matrix multiplication of Eq. 6 or 7 above).

In this regards it should be understood that in some embodiments of the present invention, the data input module 310 is adapted to obtain input data indicative of the impedance matrix Q (e.g. of a base plane of the patterned structure). The matrix multiplication processing module 340 multiplies the general electromagnetic propagation matrix $[\wedge]$ by the impedance matrix Q thereby obtaining the scattering matrix R of the patterned structure S.

In some embodiments the scattering matrix is indicative of at least one of reflection, transmission, and/or scattering, of electromagnetic radiation from the patterned structure as function of at least one of the following parameters:
  Wavelength content $\lambda$ of the incident electromagnetic radiation IB;
  Polarization P of the incident electromagnetic radiation IB;
  Angle of incidence $\theta_{in}$ of the electromagnetic radiation IB on the patterned structure; and
  Angle of collection $\theta_{out}$ (diffraction order) of electromagnetic radiation reflected or scattered from the patterned structure.

Figure 4A:
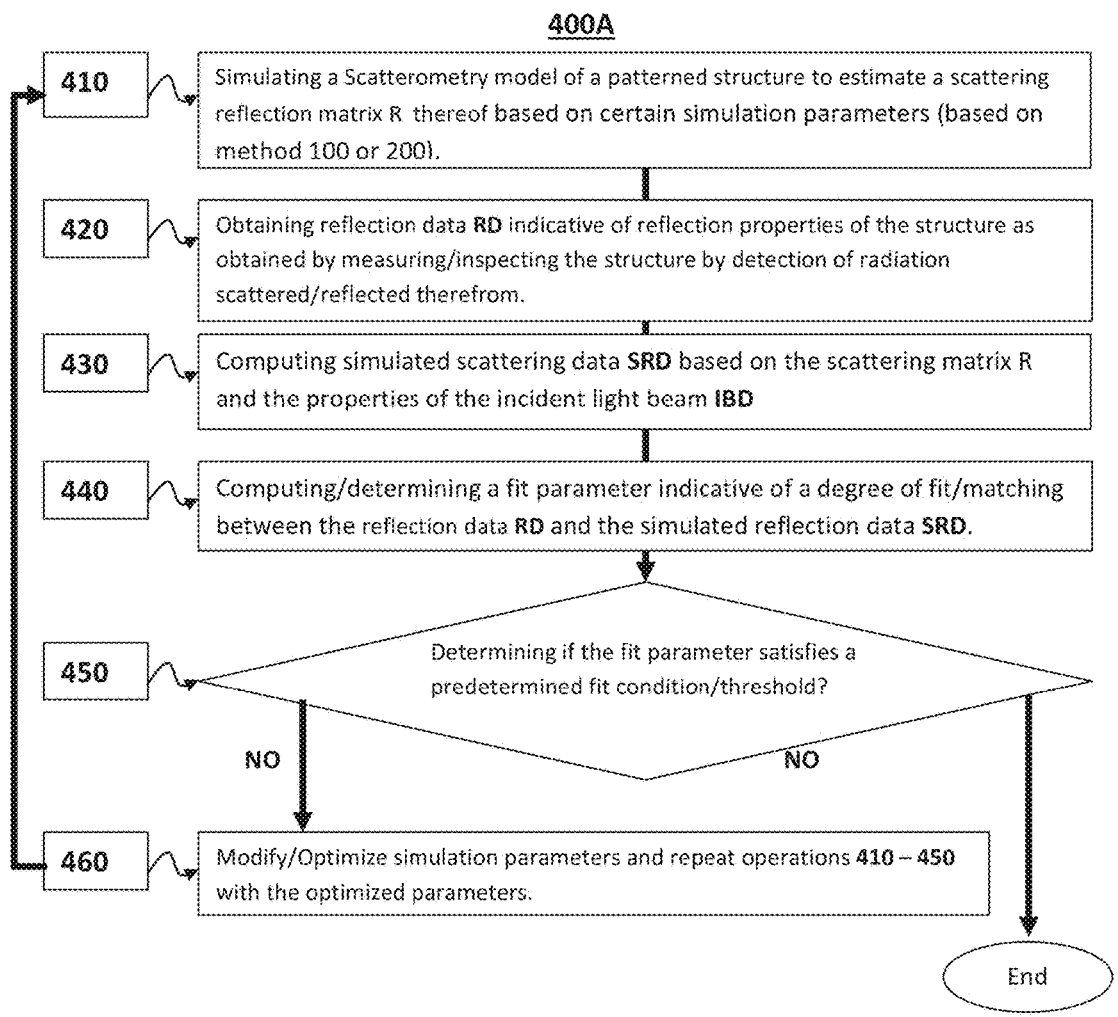
FIGS. 4A and 4B show respectively examples of a flow chart 400A and a block diagram 400B illustrating a method and a Scatterometry system for processing and optimizing scattering matrix based on response signals measured from the patterned structure S.
Figure 4B:
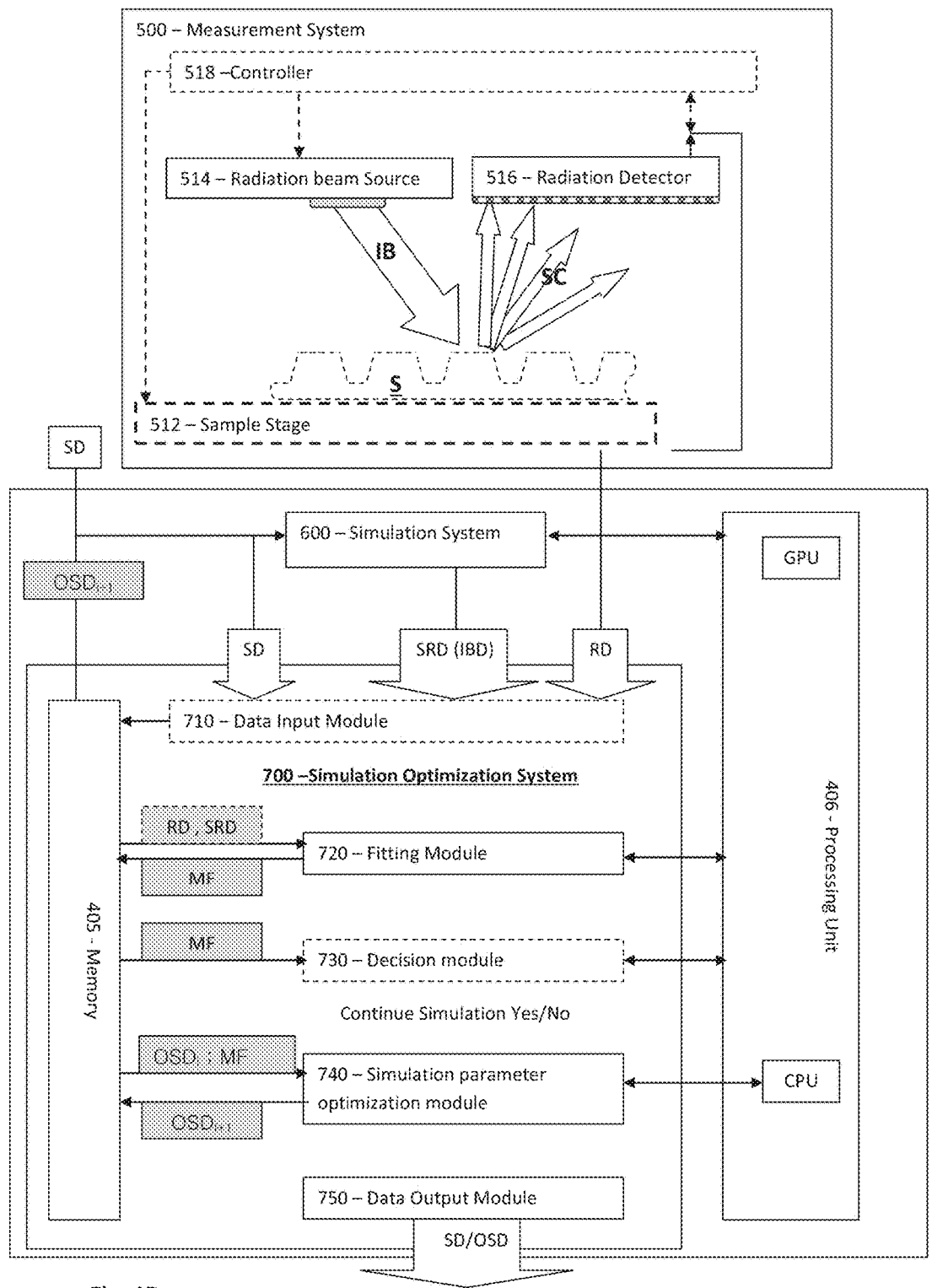

Reference is made together to FIGS. 4A and 4B, which are a flow chart 400A and a block diagram 400B respectively illustrating a method and system for use in Scatterometry measurements of a patterned structure S. It should be noted that although these examples illustrate real-time measurement mode, it should be understood that the principles of the invention (i.e. the above-described method) can be used for library creation, as well as a combined mode including both.

The system 400B includes a processor module 306 including a GPU architecture processor GPU, a CPU architecture processor CPU, and a memory module 405. Certain of the differentiating features between such GPU and CPU architecture processors were listed above. The system 400B includes a simulation system 600, and a simulation optimization system 700, and is connectable to a measurement system 500 (online mode) or an external storage device (offline mode) for receiving measurement data.

The simulation system 600 is configured and operable for operating the GPU architecture processor GPU for simulating the scattering from a patterned structure S based on given (selected) parametric space point defined by scatterometry model SD (or based on optimized/modified parametric space point $OSD_I$ as described below). The model SD includes simulation parameters indicative of the patterned structure's features geometry and materials, and possibly also corresponds to a certain measurement scheme characterized by certain properties (wavelengths/polarization/angle of incidence) of the inspection radiation beam IB, and properties of the detection of the scattered radiation from SC the patterned structure by the metrology system. For instance, the simulation system 600 may be configured and operable for carrying out rigorous coupling wave analysis (RCWA) of the patterned structure S based on certain simulation parameters, to provide simulated data SRD indicative of an estimated/simulated scattering matrix R of the patterned structure S. The simulation system 600 may be for example configured and operable similarly to the system 300 described above with reference to FIG. 3. To this end the simulation system 600 carries out operation 410 of method 400A and estimates the scattering/reflection matrix R of the patterned structure S based on certain simulation parameters.

The simulation optimization module/system 700 is connectable for receiving Scatterometry measurement results obtained from an external system which may be the measurement system 500 or storage device, from which the Scatterometry measurement results can be obtained. To this end the simulation optimization module/system 700 is adapted for carrying out operation 420 of method 400A for obtaining measurement results data RD indicative of measured scattering (reflection/transmission) response of the patterned structure S, as the later are measured by system 500. Such measurement system 500, as illustrated for example in FIG. 4B, may include: electromagnetic radiation beam source 514 (e.g. optical/light source) configured for producing electromagnetic radiation IB (e.g. optical/light radiation) directed along illumination channel to be incident on the patterned structure; a radiation detector 516 (e.g. optical/photo detector) capable of detecting scattered radiation SC propagating in a detection channel (e.g. reflected/transmitted) from the patterned structure S, and possibly also a controller 518 connectable to the radiation detector 516 and optionally also to the radiation beam source 514, and adapted to obtain data indicative of the detected scattered radiation SC. Optionally, the controller 518 provides the measurement scheme data (e.g. wavelength, polarization and/or angle of incidence) used in the system 500. The configuration and operation of the measurement system may be of any known suitable type, and do not form part of the present invention, and therefore need not be specifically described.

The simulation optimization module 700 may include a data input module 710 capable of receiving the Scatterometry measurement results data RD which is indicative of the scattering and/or reflection and/or transmission, of the patterned structure as a function of at least one parameter of the measurement scheme. The input data module 710 may also be connectable to the simulation system 600 for receiving therefrom the simulated scattering matrix R and/or the respective simulated response signals SRD. In some embodiments operation 430 is carried out to compute the simulated scattering response signals SRD by computing the values of the scattering matrix R (which is obtained in 410) and using the measurement scheme data. The measured response signals RD and the simulated response signals SRD may be stored in memory 405.

The simulation optimization module 700 includes a fitting module 720 configured and operable to carry out operation 440 of method 400A, to process the measured data RD and the simulated data SRD to determine a fit parameter MF (e.g. figure of Merit (Merit function)) indicative of a degree of matching between the simulated/estimated response data (e.g. included in SRD) and the measured data (e.g. included in RD).

In certain embodiments of the present invention, in operation 440, the simulation optimization module 700 is configured and operable to compute/process the degree of fit (merit function) between the simulated and measured responses, SRD and RD, by the CPU architecture processor CPU (and not the GPU architecture processor). In this regards it should be noted that the inventors of the present invention have noted that CPU architecture processors are superior to GPU architecture processors with regards to serial type of processing. Accordingly, utilizing CPU architecture processors to perform the fitting/merit-function computations may be more efficient and less time consuming as compared to performance of these operations by a GPU architecture processor.

In operation 450 the simulation optimization module 700 determining whether the fit parameter MF satisfies a certain best fit condition FC (e.g. fit threshold). For instance the simulation optimization module 700 may include a decision module 730 adapted to retrieve data indicative of the predetermined fit condition FC from the memory 405, and determine whether it is satisfied by the fit parameter MF obtained in 440 (e.g. determine whether the merit function computed in 440 is below a merit function threshold (e.g. which presents a predetermined fit condition FC).

It should be noted that operation 430 may be performed for multiple points in the parametric space and the results may be stored presenting the library for further use in actual measurements on patterned structures.

Alternatively or additionally a real time regression processing may be used to optimize the simulated scattering response for a given set of parameters. In this case, operation 460 may be carried out to modify/optimize the scatterometry model $OSD_{I+1}$. Then the CPU architecture processor is operated to carry out (repeat) operations 410 to 450 with the optimized scatterometry model $OSD_{I+1}$ (e.g. to carry out iterative optimization by until the fitting parameter MF, satisfies the predetermined fit condition FC).

To this end the simulation optimization system 700 may include a parameter optimization module 740 that is configured and operable to modify the certain simulation parameters, in accordance with a certain optimization scheme, repeating the simulating procedure to determine the scattering matrix/properties R of the patterned structure S based on the optimized simulation parameters, and then repeating determination of the fit parameter MF and whether it satisfies the predetermined fitting condition FC.

As will be appreciated by those versed in the art, the optimization module 740 may be configured and operable for utilizing the CPU architecture processor for performing processing associated therewith, optimizing the simulation parameters by carrying out parameter optimization based on any one or more of the following optimization techniques: Simplex optimization; Levenberg-Marquardt algorithm (LMA); Newton optimization, Guess-Newton, Gradient descend, Stochastic gradient descend, Conjugate gradient, Machine learning methods.

It should be noted that the system 400B provides optimal results in terms of computation time requirements. This is achieved by using the GPU architecture processor to simulate the scattering matrix (operation 410) with improved efficiency. Additionally, CPU architecture processor CPU may be used for performing at least one of the fitting operation 440 and the parameter optimization operation 460 with improved efficiency. It should be noted that in some embodiments the operation 440 and 460, may be performed by the GPU architecture processor, in which case with somewhat reduced performance, and more lengthy computational time is obtained.

The invention claimed is:

1. A method for use in simulating scatterometry response of a patterned structure for scatterometry analysis for the patterned structure, the method comprising:
   (a) providing input data comprising: a scatterometry model of the patterned structure comprising a selected number of virtual segment data pieces indicative of a respective number of virtual segments of the patterned structure along Z-axis through the structure; and data indicative of one or more parameters of a measurement scheme used in scatterometry measurements on the patterned structure;
   (b) processing each of the virtual segment data pieces, said processing comprising:
      i) determining a matrix $[\Omega_n]$ comprising Z-axis derivatives of electromagnetic fields' response of the segment to incident field based on Maxwell's equations' solution;
      ii) transforming said matrix $[\Omega_n]$ into an approximated response matrix $[\wedge_n]$ corresponding to the electromagnetic field interaction between two different points spaced along the Z-axis, said transforming comprising embedding said matrix $[\Omega_n]$ in a series expansion of said matrix exponential term $[\wedge_n]$;
   (c) determining a general propagation matrix $[\wedge]$ by carrying out multiplication of the approximated response matrices $\{[\wedge_n]\}$; and
   (d) utilizing the general propagation matrix $[\wedge]$ to determine a scattering matrix for the patterned structure;
   (e) applying said input data indicative of the one or more parameters of the measurement scheme to said scattering matrix, thereby obtaining one or more simulated scatterometry signatures indicative of simulated response signals from the patterned structure, wherein the simulated scatterometry signature is a function of at least one parameter of the measurement scheme and corresponds to one or more points in a certain parametric space of said scatterometry model; and
   (f) measuring one or more parameters of actual patterned structures, utilizing any of the obtained simulated scatterometry signatures of simulated response signals, for patterned structure process control that includes fitting measured signals of the actual patterned structures with any of the simulated response signals.

2. The method of claim 1, wherein at least the step (ii) is carried out by a GPU architecture processor.

3. The method of claim 2, wherein said GPU has at least one of the following configurations: a standard GPU, general purpose GPU (GPGPU), and a Many-Integrated-Core Architecture (MIC) processor.

4. The method of claim 1, wherein at least the steps (ii) and (c) are carried out by a GPU architecture processor.

5. The method of claim 1, wherein said scatterometry model comprising a set of structure parameters spanning the certain parametric space; the scattering matrix of the pattern structure corresponding to the point in the parametric space defined by the model, the method comprising carrying out said determination of the scattering matrix for a plurality of points in said parametric space respectively, thereby obtaining data indicative of a plurality of simulated scattering response signals for said plurality of points respectively.

6. The method of claim 5, further comprising comparing measured scatterometry response signals of the patterned structure with the simulated scattering response signals, and determining one or more parameters of the structure based on a best fit condition.

7. The method of claim 1, wherein the measurement scheme is characterized by at least one of illumination and detection conditions.

8. The method of claim 7, wherein the at least one of illumination and detection conditions comprises at least one of polarization and diffraction order being collected.

9. The method of claim 1, wherein said scattering matrix corresponds to an illuminating wavelength, said processing being carried out for each of at least two illuminating wavelengths.

10. The method of claim 1, wherein said series expansion includes at least one of Taylor Expansion and polynomial expansion.

11. The method of claim 1, wherein the determination of the scattering matrix comprises utilizing an impedance matrix of media surrounding the patterned structure and said general propagation matrix.

12. A system for use in simulating scatterometry response of a patterned structure for scatterometry analysis for the patterned structure, the system comprising:
 a data input module for receiving input data comprising a scatterometry model data of a patterned structure comprising a selected number of virtual segment data pieces indicative of a respective number of segments of the patterned structure along Z-axis through the structure; and data indicative of one or more parameters of a measurement scheme used in scatterometry measurements on the patterned structures;
 a matrix data processing module configured for processing each of the segment data pieces and determining a matrix $[\Omega_n]$ comprising Z-axis derivatives of electromagnetic fields' response of the segment to incident field based on Maxwell's equations' solution, and transforming said matrix $[\Omega_n]$ into an exponential term $[\wedge_n]$ corresponding to electromagnetic field interaction between two different points spaced along the Z-axis, said transforming comprising embedding said matrix $[\Omega_n]$ in a series expansion of said matrix exponential term $[\wedge_n]$;
 a matrix multiplication processing module adapted for multiplying the approximated response matrices $\{[\wedge_n]\}$ corresponding to all the segment data pieces and determining a general propagation matrix $[\wedge]$,
 a scattering matrix generator configured for utilizing the general propagation matrix $[\wedge]$ and determining a scattering matrix of the patterned structure, and
 a simulation system configured to apply said input data indicative of the one or more parameters of the measurement scheme to said scattering matrix, thereby obtaining one or more simulated scatterometry signatures indicative of simulated response signals from the patterned structure, wherein the simulated scatterometry signature is a function of at least one parameter of the measurement scheme and corresponds to one or more points in a certain parametric space of said scatterometry model; and to measure one or more parameters of actual patterned structures, utilizing any of the obtained simulated scatterometry signatures of simulated response signals, for patterned structure process control that includes fitting measured signals of the actual patterned structures with any of the simulated response signals.

13. The system of claim 12, comprising a GPU architecture processor comprising at least said matrix data processing module.

14. The system of claim 12, wherein said scatterometry model comprises a set of structure parameters spanning the certain parametric space; the scattering matrix of the pattern structure corresponding to a point in the parametric space defined by the model, the system comprising an optimization module operable for determining the scattering matrix for a plurality of points in said parametric space respectively, thereby obtaining data indicative of a plurality of simulated scattering response signals for said plurality of points respectively.

15. The system of claim 12, wherein said simulation system is a part of the scattering matrix generator, which is further configured for said determination of the simulated scattering response signals for the patterned structure using said scattering matrix.

16. The system of claim 15, wherein said data indicative of the measurement scheme comprises at least one of illumination and detection conditions.

17. The system of claim 15, further comprising a fitting module adapted for comparing measured scatterometry response signals of the patterned structure with the simulated scattering response signals, and determining one or more parameters of the structure based on a best fit condition.

18. The system of claim 15, further comprising an optimization module adapted for carrying out a real time regression processing to optimize the simulated scattering response for a given set of parameters.

19. A non-transitory program storage device readable by machine, tangibly embodying a program of instructions executable by the machine to perform a method for use in scatterometry analysis for a patterned structure, comprising:
 (a) providing a scatterometry model of a patterned structure comprising a selected number of virtual segment data pieces indicative of a respective number of segments of the patterned structure along Z-axis through the structure; and
 (b) processing each of the virtual segment data pieces, said processing comprising:
  i) determining a matrix $[\Omega_n]$ comprising Z-axis derivatives of electromagnetic fields' response of the segment to incident field based on Maxwell's equations' solution;
  ii) transforming said matrix $[\Omega_n]$ into an approximated response matrix $[\wedge_n]$ corresponding to the electromagnetic field interaction between two different points spaced along the Z-axis, said transforming comprising embedding said matrix $[\Omega_n]$ in a series expansion of said matrix exponential term $[\wedge_n]$;
 (c) determining a general propagation matrix $[\wedge]$ by carrying out multiplication of the approximated response matrices $\{[\wedge_n]\}$;
 (d) utilizing the general propagation matrix $[\wedge]$ to determine a scattering matrix for the patterned structure;

(e) applying data indicative of a measurement scheme to said scattering matrix, thereby obtaining simulated data comprising one or more simulated scatterometry signatures indicative of simulated response signals from the patterned structure, the simulated scatterometry signature being a function of at least one parameter of the measurement scheme and corresponding to one or more points in a certain parametric space of said scatterometry model; and (f) measuring one or more parameters of actual patterned structures, utilizing any of the obtained simulated scatterometry signatures of simulated response signals, for patterned structure process control that includes fitting measured signals of the actual patterned structures with any of the simulated response signals.

* * * * *